US009513357B2

(12) United States Patent
Hsiao et al.

(10) Patent No.: US 9,513,357 B2
(45) Date of Patent: Dec. 6, 2016

(54) COMPREHENSIVE CARDIOVASCULAR ANALYSIS WITH VOLUMETRIC PHASE-CONTRAST MRI

(75) Inventors: Albert Hsiao, Menlo Park, CA (US); Shreyas S Vasanawala, Stanford, CA (US); Marcus T. Alley, Palo Alto, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 183 days.

(21) Appl. No.: 14/118,964

(22) PCT Filed: Jul. 5, 2012

(86) PCT No.: PCT/US2012/045575
§ 371 (c)(1),
(2), (4) Date: Nov. 20, 2013

(87) PCT Pub. No.: WO2013/006709
PCT Pub. Date: Jan. 10, 2013

(65) Prior Publication Data
US 2014/0112564 A1    Apr. 24, 2014

Related U.S. Application Data

(60) Provisional application No. 61/571,908, filed on Jul. 7, 2011.

(51) Int. Cl.
*G06K 9/00*   (2006.01)
*G01R 33/56*  (2006.01)
(Continued)

(52) U.S. Cl.
CPC ........... *G01R 33/56* (2013.01); *G01R 33/5608* (2013.01); *G01R 33/56316* (2013.01); *G01R 33/56518* (2013.01); *G06T 7/0012* (2013.01); *G01R 33/546* (2013.01)

(58) Field of Classification Search
None
See application file for complete search history.

(56) References Cited

U.S. PATENT DOCUMENTS 5,115,812 A   5/1992  Sano
6,934,698 B2  8/2005  Judd
(Continued)

FOREIGN PATENT DOCUMENTS

JP    H02-147048    6/1990
JP    H05-84231     6/1991
(Continued)

OTHER PUBLICATIONS

Bock et al., "Optimized pre-processing of time-resolved 2D and 3D phase contrast MRI data", Porc. Intl. Soc. Mag. Reson. Med. 15 (2007).*

(Continued)

*Primary Examiner* — Soo Park
(74) *Attorney, Agent, or Firm* — Lumen Patent Firm

(57) ABSTRACT

Processing techniques of volumetric anatomic and vector field data from volumetric phase-contrast MRI on a magnetic resonance imaging (MRI) system are provided to evaluate the physiology of the heart and vessels. This method includes the steps of: (1) correcting for phase-error in the source data, (2) visualizing the vector field superimposed on the anatomic data, (3) using this visualization to select and view planes in the volume, and (4) using these planes to delineate the boundaries of the heart and vessels so that measurements of the heart and vessels can be accurately obtained.

24 Claims, 15 Drawing Sheets

(51) Int. Cl.
*G01R 33/563* (2006.01)
*G01R 33/565* (2006.01)
*G06T 7/00* (2006.01)
*G01R 33/54* (2006.01)

(56) References Cited

U.S. PATENT DOCUMENTS

| | | | |
|---|---|---|---|
| 7,254,436 | B2 | 8/2007 | Judd |
| 7,457,656 | B2 | 11/2008 | Judd |
| 7,668,835 | B2 | 2/2010 | Judd |
| 7,958,100 | B2 | 6/2011 | Judd |
| 8,055,636 | B2 | 11/2011 | Judd |
| 8,166,381 | B2 | 4/2012 | Judd |
| 2002/0146159 | A1 | 10/2002 | Nolte |
| 2005/0238233 | A1 | 10/2005 | Mulet Parada |
| 2006/0106877 | A1 | 5/2006 | Lee |
| 2007/0061460 | A1 | 3/2007 | Khan |
| 2008/0054900 | A1 | 3/2008 | Polzin |
| 2009/0226064 | A1 | 9/2009 | El Fakhri |
| 2010/0085052 | A1 | 4/2010 | Johnson et al. |
| 2010/0094122 | A1 | 4/2010 | Kiraly |
| 2010/0280352 | A1 | 11/2010 | Ionasec |
| 2011/0230756 | A1 | 9/2011 | Axel Odeen et al. |
| 2012/0076380 | A1* | 3/2012 | Guhring ............ A61B 5/0263 382/131 |
| 2012/0271156 | A1 | 10/2012 | Bi |
| 2013/0259351 | A1 | 10/2013 | Wiemker, II |

FOREIGN PATENT DOCUMENTS

| WO | WO00/67185 | 11/2000 |
|---|---|---|
| WO | WO2010/038138 | 4/2010 |

OTHER PUBLICATIONS

Lankhaar et al., "Correction of phase offset errors in main pulmonary artery flow quantification", Journal of Magnetic Resonance Imaging 22:73-79 (2005).*

Hsiao et al. Improved cardiovascular flow quantification with time-resolved volumetric phase-contrast MRI. Pediatr. Radiol. 2011(41) 711-720.

Frydrychowicz et al. Four-dimensional phase contrast magnetic resonance angiography: potentional clinical applications. European Journal of Radiology 80(2011) 24-35.

Markl et al. Generalized Modeling of Gradient Field Non-Linearities and Reconstruction of Phase Contrast MRI measurements. Proc. Intl. Mag. Reson. Med. 11 (2003) 1027.

Giese et al. Optimized Pre-Processing Strategy for the Correction of Gradient Field Inhomogeneities in 3D-PC-MRI. Proc. Intl. Mag. Reson. Med. 16 (2008) 1371.

Delles et al. Quadratic phase offset error correction of velocity-encoded magnetic resonance imaging data. Int. J. CARS 2009(4) Suppl. 1 S10-11.

Markl et al. Generalized Reconstruction of Phase Contrast MRI: Analysis and Correction of the Effect of Gradient Field Distortions. Mag. Reson. in Med. 2003(50):791-801.

Hsiao et al (2011). Improved cardiovascular flow quantification with time-resolved volumetric phase-contrast MRI. Pediatr Radiol. Jun. 2011;41(6):711-20.

Peeters, "Analysis and Correction of Gradient Nonlinearity and B0 Inhomogeneity Related Scaling Errors in Two-Dimensional Phase Contrast Flow Measurements," Magnetic Resonance in Medicine 53:126-133, 2005.

* cited by examiner

COMPREHENSIVE CARDIOVASCULAR ANALYSIS WITH VOLUMETRIC PHASE-CONTRAST MRI

This application is a US National Stage under USC 371 of PCT/US2012/045575 filed on Jul. 5, 2012. PCT/US2012/045575 filed on Jul. 5, 2012 claims the benefit of U.S. Provisional Patent Application 61/571,908 filed on Jul. 7, 2011.

FIELD OF THE INVENTION

This invention relates to methods and systems to perform measurements of the heart and vessels, including measurements of blood flow and motion, using volumetric data obtained from an MRI that includes anatomic (magnitude) and vector field (phase) data from a volumetric phase-contrast MRI pulse sequence.

BACKGROUND OF THE INVENTION

Phase-Contrast MRI Phase-Error Correction

Volumetric phase-contrast magnetic resonance imaging (4DPC MRI) is a promising technique for obtaining data of periodic motion and blood flow. The usefulness of the technique has been limited, however, by the lack of methods for addressing phase-offset errors, presumed to be related to uncompensated eddy-currents during the MRI acquisition. Techniques for addressing phase-offset errors in volumetric data have relied on techniques directly adapted from planar, two-dimensional PC-MRI.

Two-dimensional phase-contrast MRI is a commonly-employed imaging method to obtain data for quantification of flow in blood vessels. In current clinical practice, this is performed with a two-dimensional planar acquisition oriented perpendicular to the axis of a vessel of interest. An image of the through-plane component of velocity is obtained over multiple phases of the cardiac cycle. To obtain volumetric flow measurements from this data, through-plane velocities are summed over a region bounded by the outline of the vessel of interest. These measurements are subject to phase-offset errors (1, 2), which are not easily corrected in this planar data.

Phase-offsets, presumed to be related to uncompensated eddy-currents, can confound measurements of blood flow. One method to correct for these errors is the manual subtraction of velocities from a selected area of stationary tissue in the slice plane. This method is the most widely used because it is the easiest to perform, but is limited because of (a) its need for manual intervention, and (b) it does not completely account for the spatial dependence of phase-error. Another proposed method to correct for these errors is the subtraction of errors measured in a stationary phantom (3). This second method however, is laborious and doubles the acquisition time on the MRI scanner, making it impractical for use in the clinical environment. A third proposed approach is to utilize automated computational procedures for phase-offset correction, the simplest of which utilizes a linear, two-dimensional model of the form $$f(x,y)=c_0+c_x x+c_y y \quad (1)$$

The parameters of this model ($c_0$, $c_x$, $c_y$) are then estimated using data from static tissues in each plane of image data, typically with a least squares regression approach (4). The resulting phase-offset model f(x,y) is then subtracted from each pixel of the velocity image.

Other two-dimensional models have also been proposed. These are of the form $$f_{n,m}(x, y) = c_0 + \sum_{i=1}^{n} c_{x,i} x^i + \sum_{i=1}^{m} c_{y,i} y^i, \quad (2)$$

where n and m are non-negative integers. This family of models includes the linear model described above, when n and m are both set to 1, but also provides an opportunity to add higher order terms to model finer spatial variations. While higher-order terms are possible, an earlier study has suggested that modeling and subtracting these terms may not improve overall accuracy (5).

Volumetric phase-contrast MRI is a related MRI technique that acquires an entire volume of data instead of a single plane, resolving a three dimensional vector field, a vector encoding motion for each voxel. Each component of velocity is subject to eddy-current-related phase offsets that can be spatially dependent, and can therefore confound quantification of flow. The typical method for correcting this data is to once again use a model of the form, $$f(x,y)=c_0+c_x x+c_y y. \quad (3)$$

This model can be separately applied to each flow direction, in each plane of data within the imaging volume, and typically is also applied separately to each temporal phase of data. This approach results in separate models for each slice of data for each gated time-point. We believe that modeling this data slice-by-slice and phase-by-phase may be unnecessarily and unpredictably inconsistent and therefore provide herein with this invention a new, more reliable method for performing correction of phase-offset errors.

Vector Field Fusion Visualization and Quantification

Volumetric phase-contrast magnetic resonance imaging is an evolving imaging technique that not only provides anatomic information about structures within the imaging volume, but also provides a vector field of data encoding motion. We recognize that this has considerable potential for evaluation of cardiac and cardiovascular diseases. Recent advances in MR imaging have now recently made it possible to acquire near-isotropic, high-resolution images while preserving high signal-to-noise of both the anatomic images and vector fields. However, no computer system yet exists that can enable clinical image interpretation and diagnosis, which is generally carried out by physicians with training in radiology and/or cardiology.

We have therefore devised a series of inventions and steps that facilitate image interpretation and quantitative analysis of 4DPC MRI data. To be used in clinical practice, we provide herein with this invention a series of inventions that allow analysis of the imaging volume, optimizing user-interaction by leveraging graphics hardware. This invention allows the user to dynamically perform the necessary visualization and computational tasks, making it feasible to perform cardiovascular examinations with the 4DPC imaging technique in the clinical environment.

SUMMARY OF THE INVENTION

Phase-Contrast MRI Phase-Error Correction

Prior methods use a computer algorithm to detect the temporal variation in phase to determine whether a given voxel represents either (a) static tissue, (b) moving fluid or tissue, or (c) noise, and assume that pixels with the least variation over time best represent static tissue. However, the proportion of static tissue voxels can be variable from patient-to-patient, can vary considerably in different regions of the human body, and can be affected by the size of the field of view. These limitations remain largely unrecognized in prior works. Since there is so much potential for incorrect assignment of static tissue based on existing approaches, we provide the use of a software program executable by a computer that enables user-guided selection of static tissue using a specific combination of image filters (see FIGS. 1A-B).

In addition to identification of static tissue voxels, it is also important to identify MRI data that misrepresents the spatial relationships of phase error. MRI data is subject to errors of spatial aliasing (spatial wrapping) when the field of view does not exceed the size of the object being imaged. These typically occur in the phase-encode and slice directions, resulting in wrapping of voxels at the edges of the imaging volume. Specific exclusion of spatially-wrapped data for phase-error correction has not been addressed in prior works. To accurately model of phase-error, we provide herein the use of a software program executable by a computer to enable user-guided exclusion of these wrapped voxels (FIG. 2A).

Existing techniques for phase-error correction of volumetric phase-contrast MRI data have been performed on a plane-by-plane basis. While less computationally intensive, these algorithms may not take advantage of the inherent spatial relationships of volumetric data. Further, there is no guarantee that such corrections are consistent across multiple adjacent planes. We provide herein the computer-executable and computer-implemented use of a volumetric phase-error model for a volume of phase-contrast data to overcome these fundamental but yet unrecognized limitations of the plane-by-plane approach.

Multiple usable three-dimensional models and temporal averaging approaches are described in more detail below. Lowest order models can efficiently model the eddy-current phase-offsets with the least computational complexity, while higher order models may provide a better fit, especially when larger imaging fields of view are utilized. When larger fields of view or higher MRI field and gradient strengths are used, the spatial dependence of phase-offset can become increasingly non-linear. However, since computational resources for correcting these problems may vary, we provide herein the use of a software program executable by a computer to decide which model to use (FIG. 2B).

Vector Field Fusion Visualization and Quantification

To make it feasible to use 4DPC MRI to perform a cardiovascular examination, we provide a sequence of computer-implemented procedures to perform visualization of this high-dimensional data on a computer, which facilitates selection of individual planes through cardiovascular structures of interest, which can then be measured or segmented. We have devised a software platform that embodies these principles, called FLOWANALYTIX. The software is tailored to cardiac and cardiovascular interpretation and integrates many necessary steps for complete qualitative and quantitative analysis of the imaging volume. These steps include:

multiplanar and volumetric visualization,
selection of planes for measurements of the vector field based on this visualization,
computationally-assisted segmentation of cardiac structures and vessels,
calculation of blood flow,
selection of diagnostic cardiac planes,
computationally-assisted segmentation of ventricular volumes, and
calculation of ventricular volumes.

To enable an efficient and accurate clinical interpretation of each 4DPC MRI data set, several specific features are required to maximize the conspicuity of pathologic blood flow, while reducing conspicuity of noise in the source image data. The algorithms for these features are detailed below.

BRIEF DESCRIPTION OF THE DRAWINGS

FIG. 1A shows raw data, while masked data retaining static tissue is shown in FIG. 1B.

In FIG. 2A the vertical and horizontal lines represent the extent of the imaging volume, which can be dynamically adjusted to exclude areas of spatial aliasing, if any is present. In FIG. 2B, the extent of the imaging volume in the slice direction can be adjusted. In addition, the type of volumetric model (product or sum), order of model (linear, square, cubic, etc.), and method of modeling can be selected.

DETAILED DESCRIPTION

Phase-Contrast MRI Phase-Error Correction

Figure 1A:
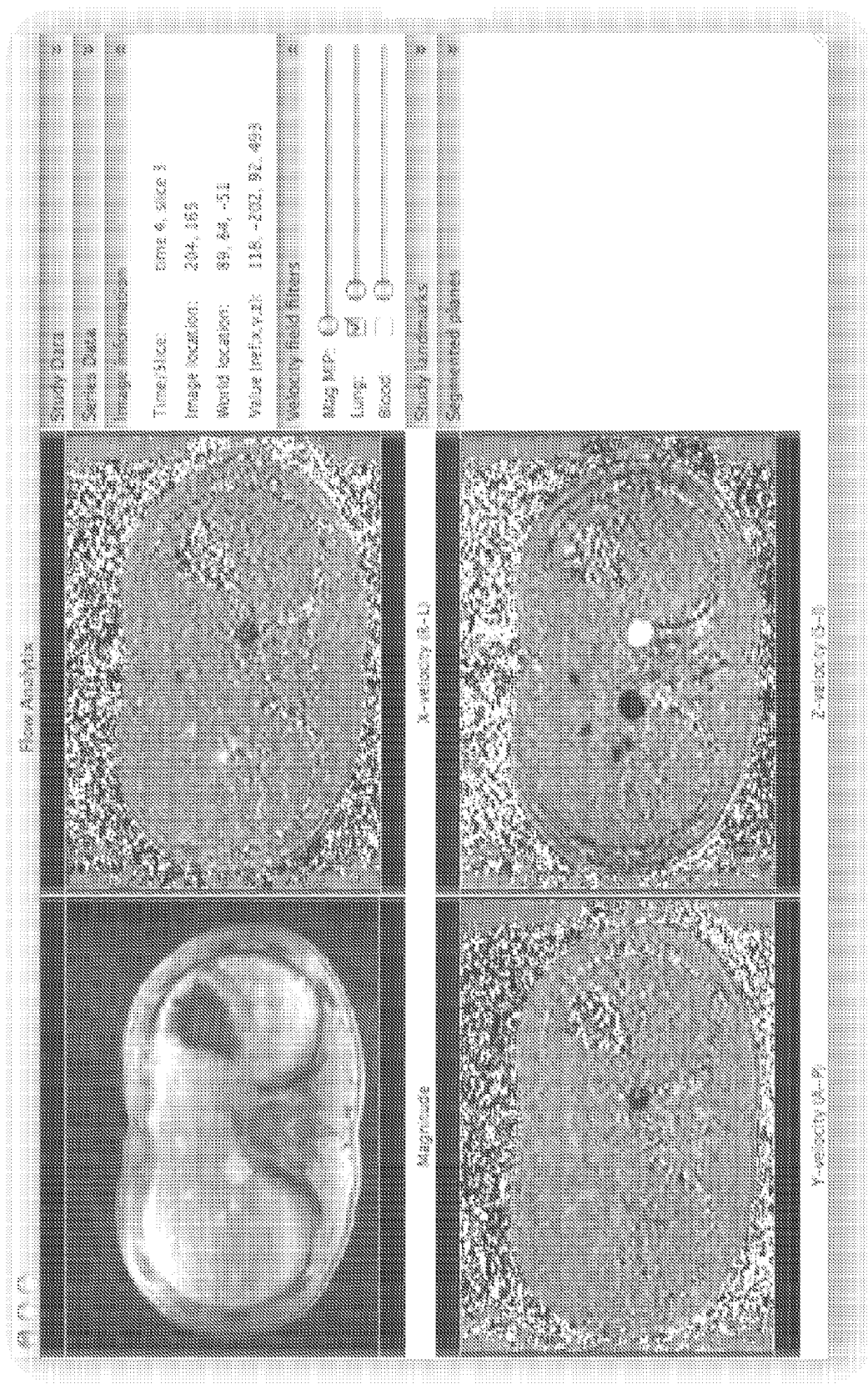
FIGS. 1A-B show screenshots of a software user-interface that allows manual selection of masks for non-static tissue according an exemplary embodiment of the present invention.
Figure 1B:
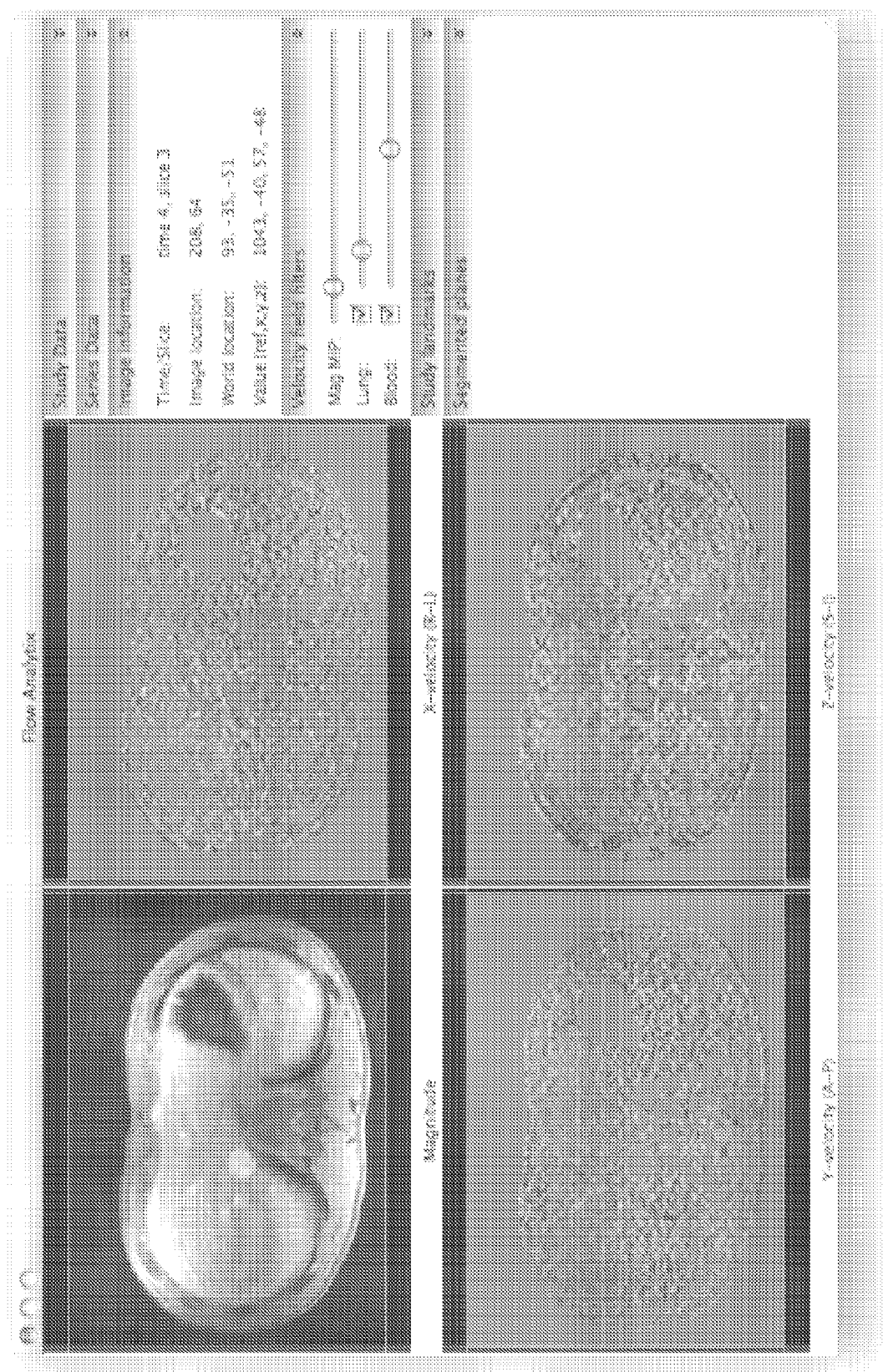
Figure 2A:
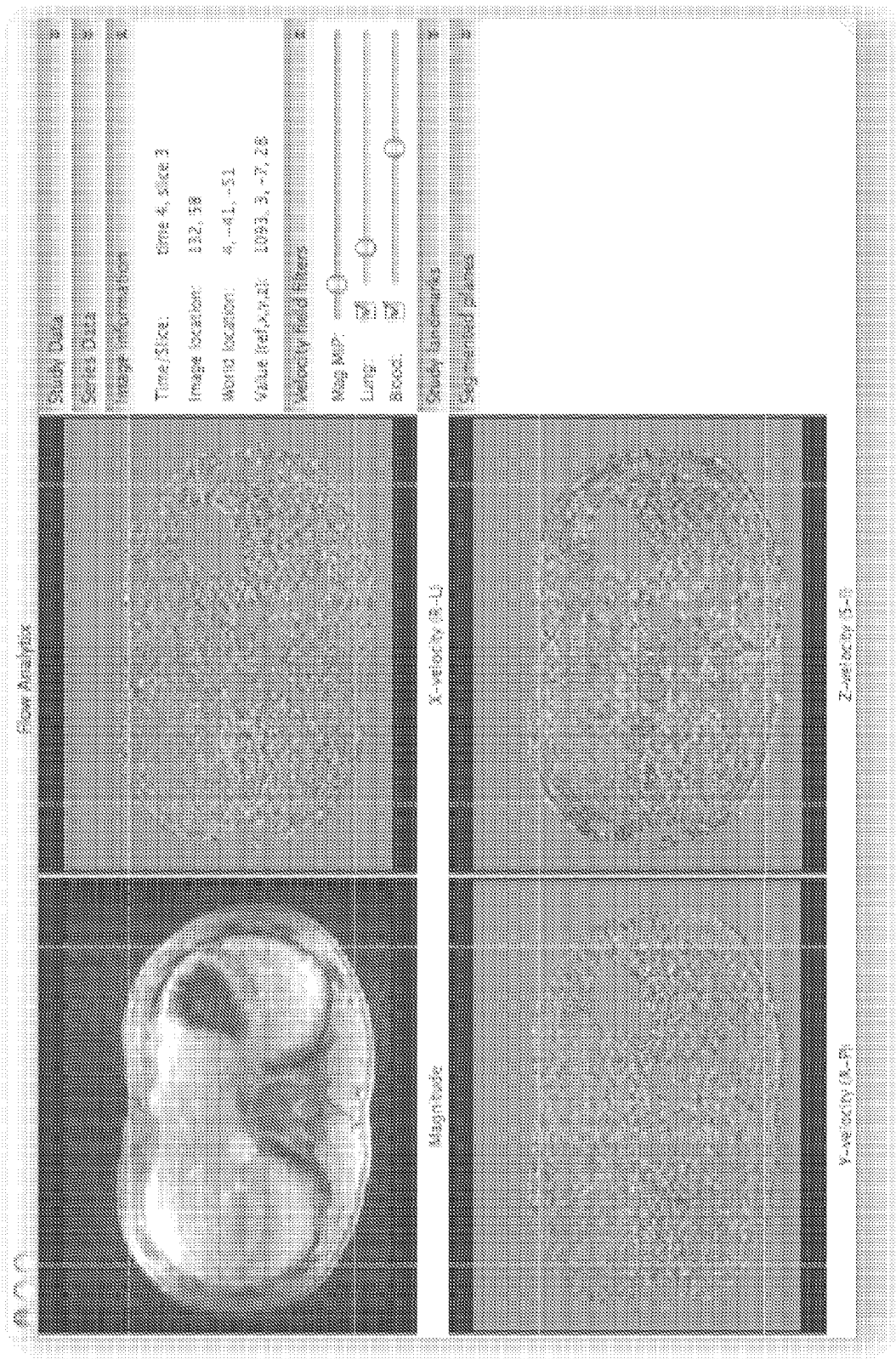
FIGS. 2A-B show screenshots of a software user-interface that allows for manual selection of a sub-volume to use for phase-offset modeling according an exemplary embodiment of the present invention.
Figure 2B:
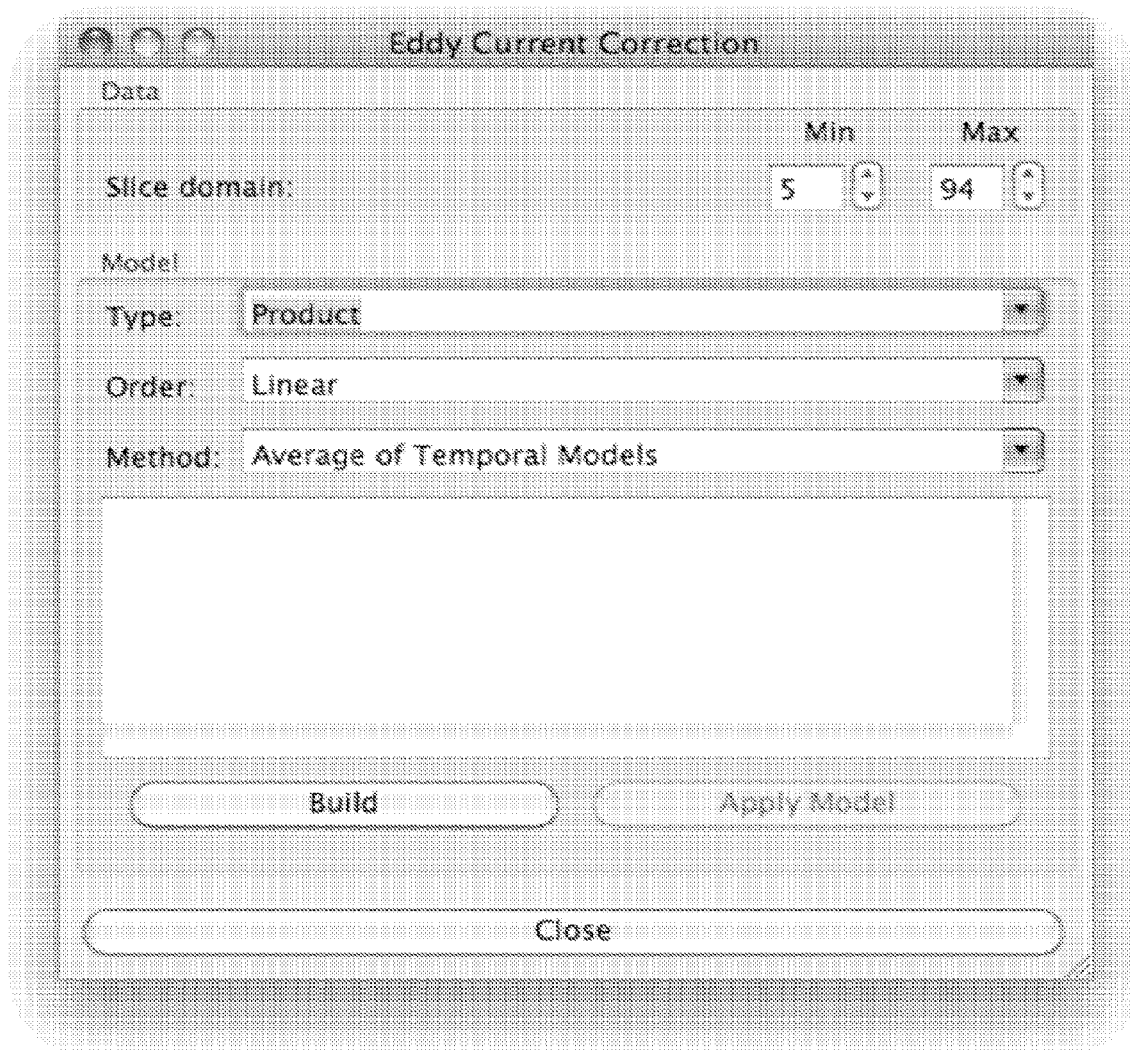
Figure 3A:
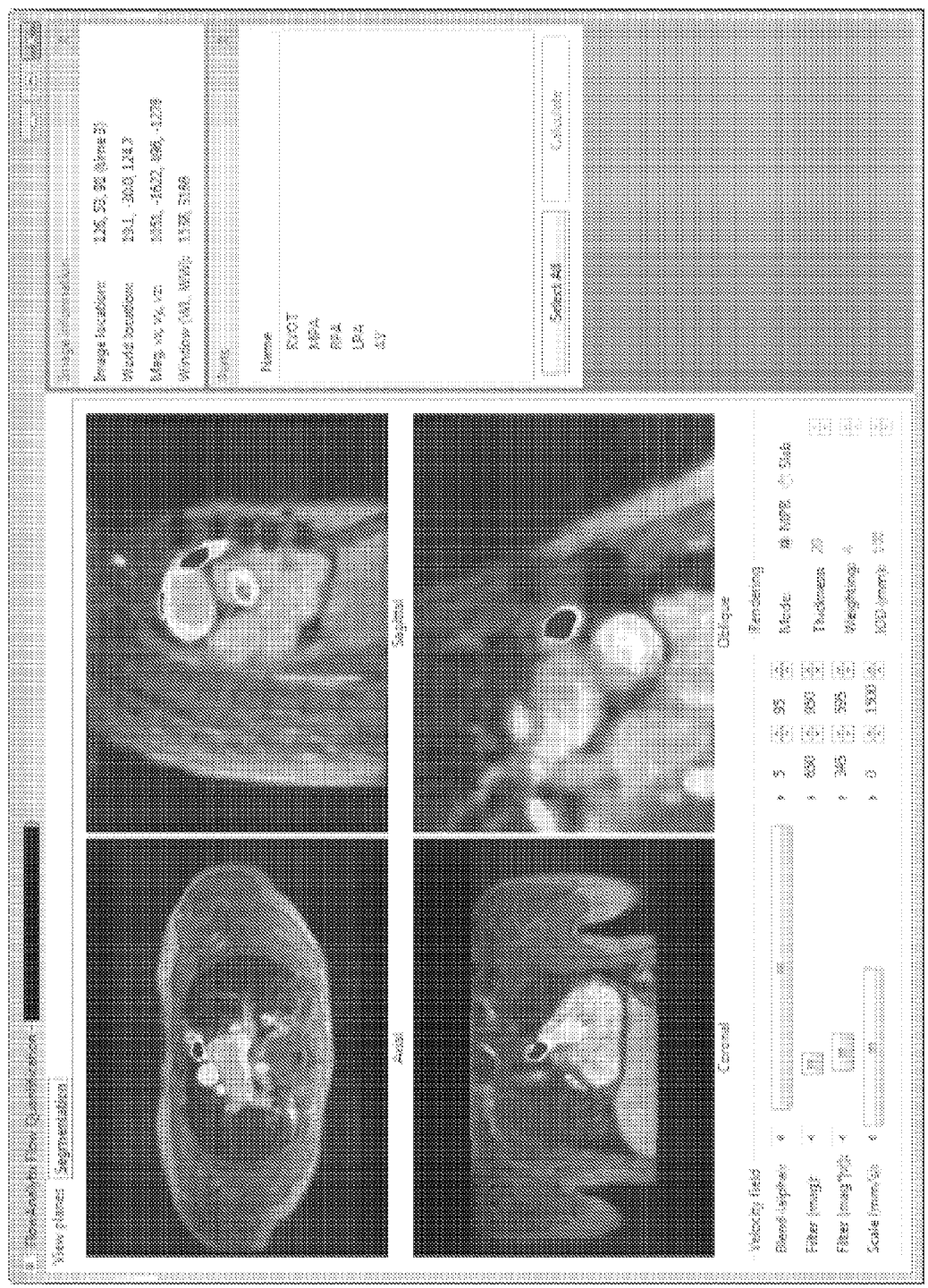
FIGS. 3A-D show screen captures (A-D) of the flow quantification viewer according an exemplary embodiment of the present invention. Reformatted axial, coronal, and sagittal views are automatically rendered and can be freely rotated and repositioned (A). Individual panes can be magnified to occupy a larger portion of the screen space (B). Vessels can be manually segmented with mouse user-interaction (C). In a second tab, nearest neighbor interpolated views of the vessel are also automatically generated to facilitate identification of velocity aliased pixels and improve segmentation accuracy (D).
Figure 3B:
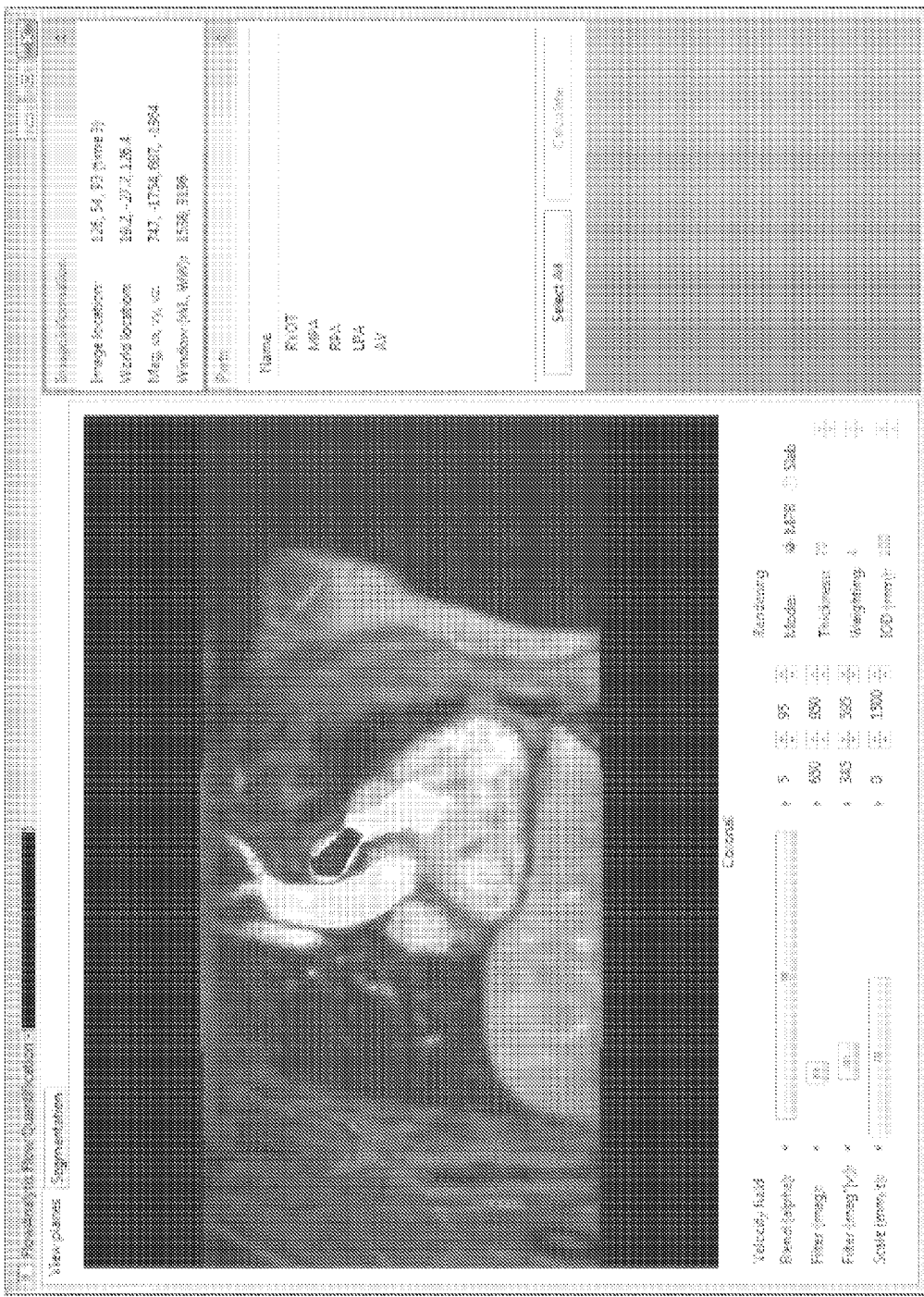
Figure 3C:
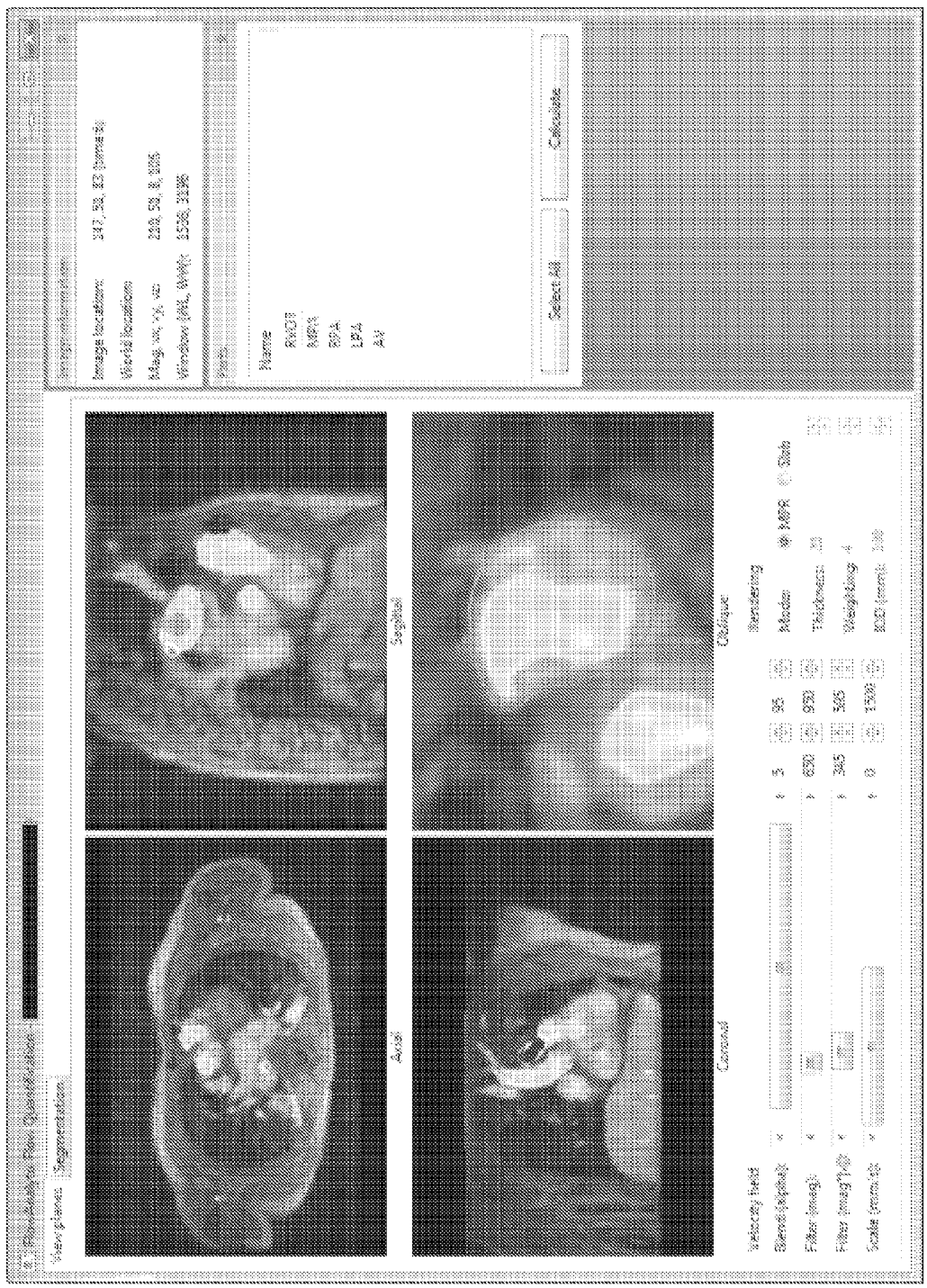
Figure 3D:
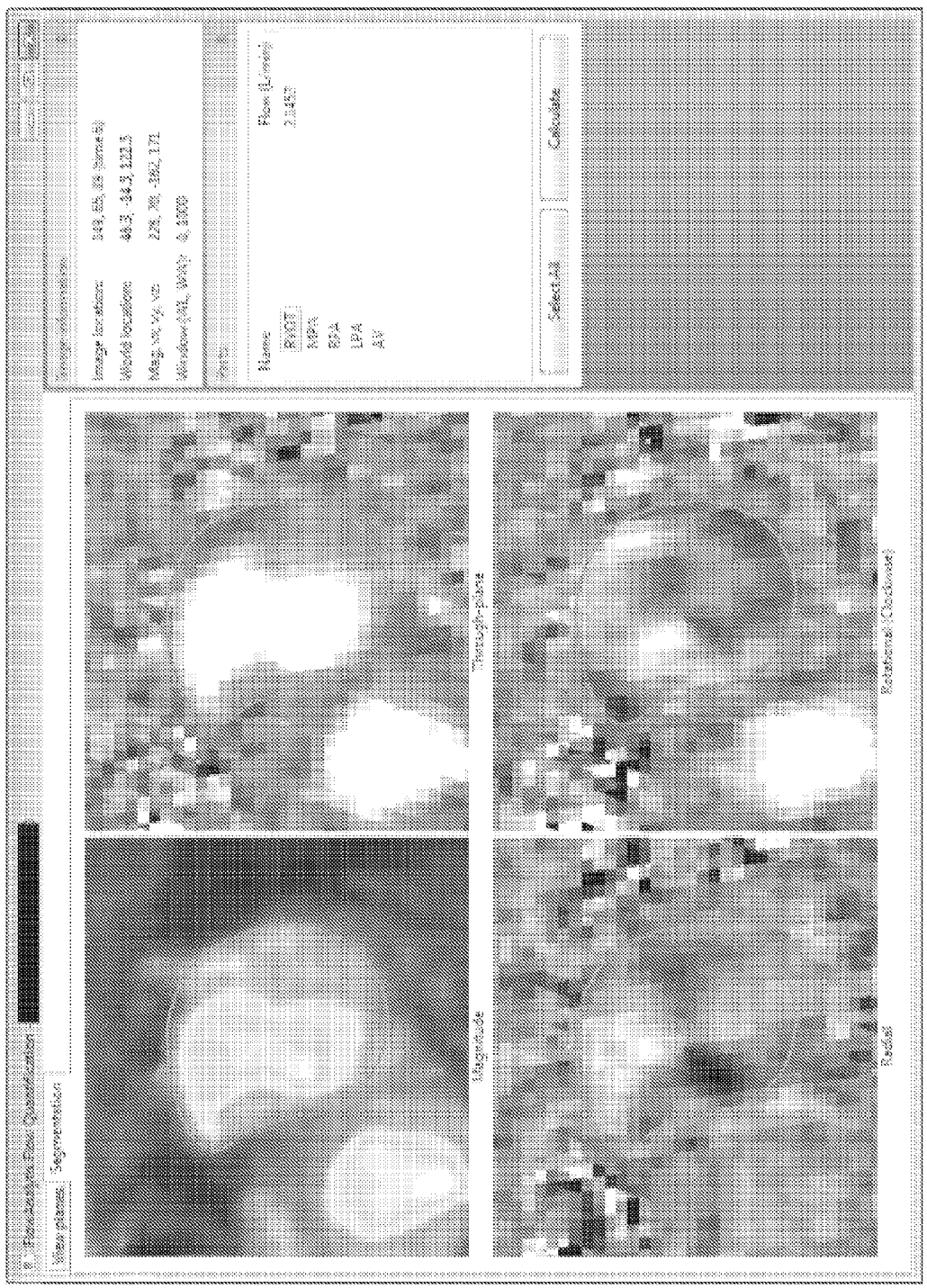
Figure 4A:
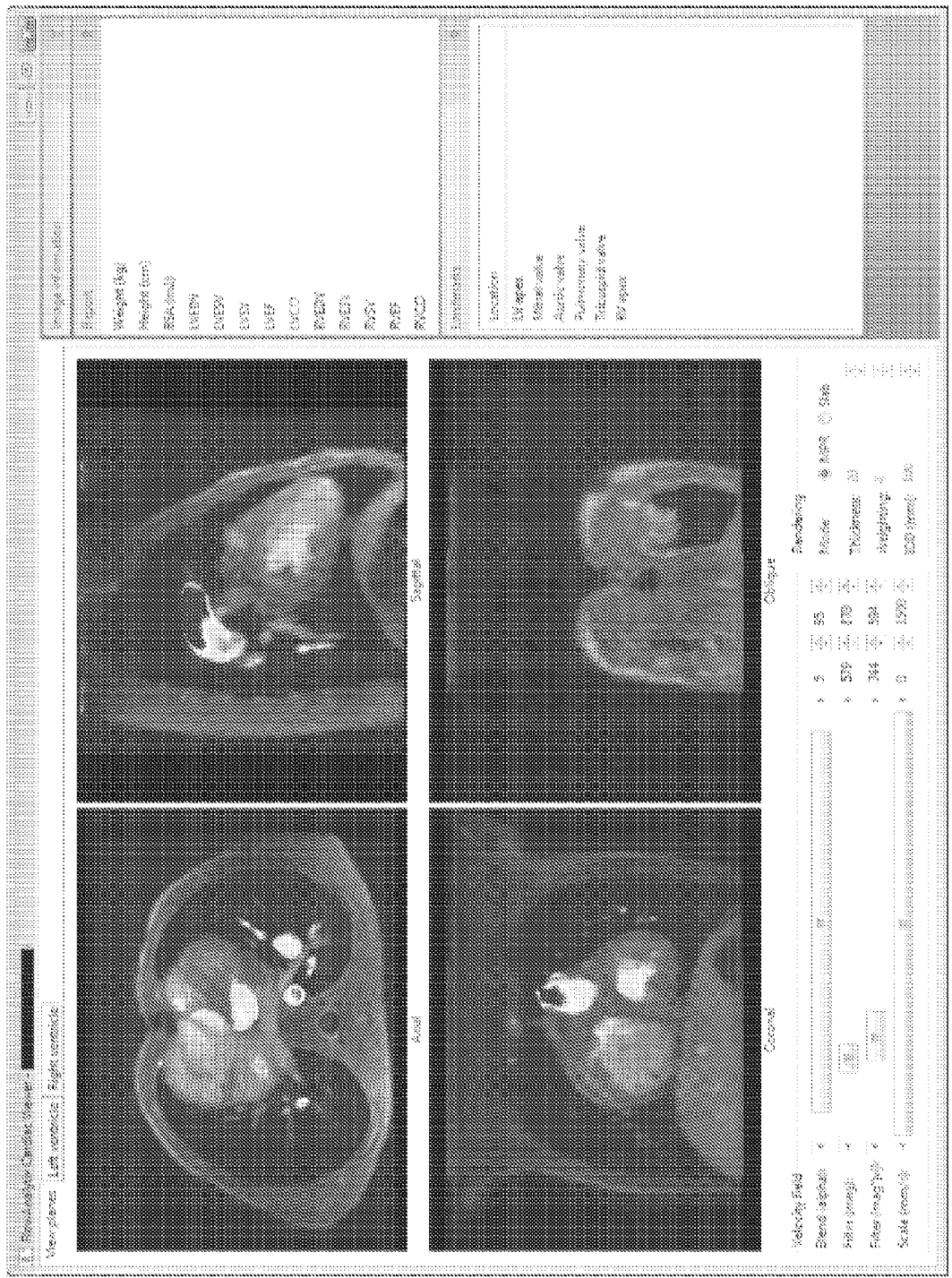
FIGS. 4A-C show screen captures of the cardiac viewer according an exemplary embodiment of the present invention. Phase (velocity) data is automatically superimposed on the multiplanar reformatted views with a color transfer function that is adjustable with sliders at the bottom of the window (A). Short-axis, long-axis, 2-, 3-, and 4-chamber views are automatically generated (B and C). Temporally-resolved landmarks can be defined for standard cardiac structures to facilitate dynamic tracking of these structures.
Figure 4B:
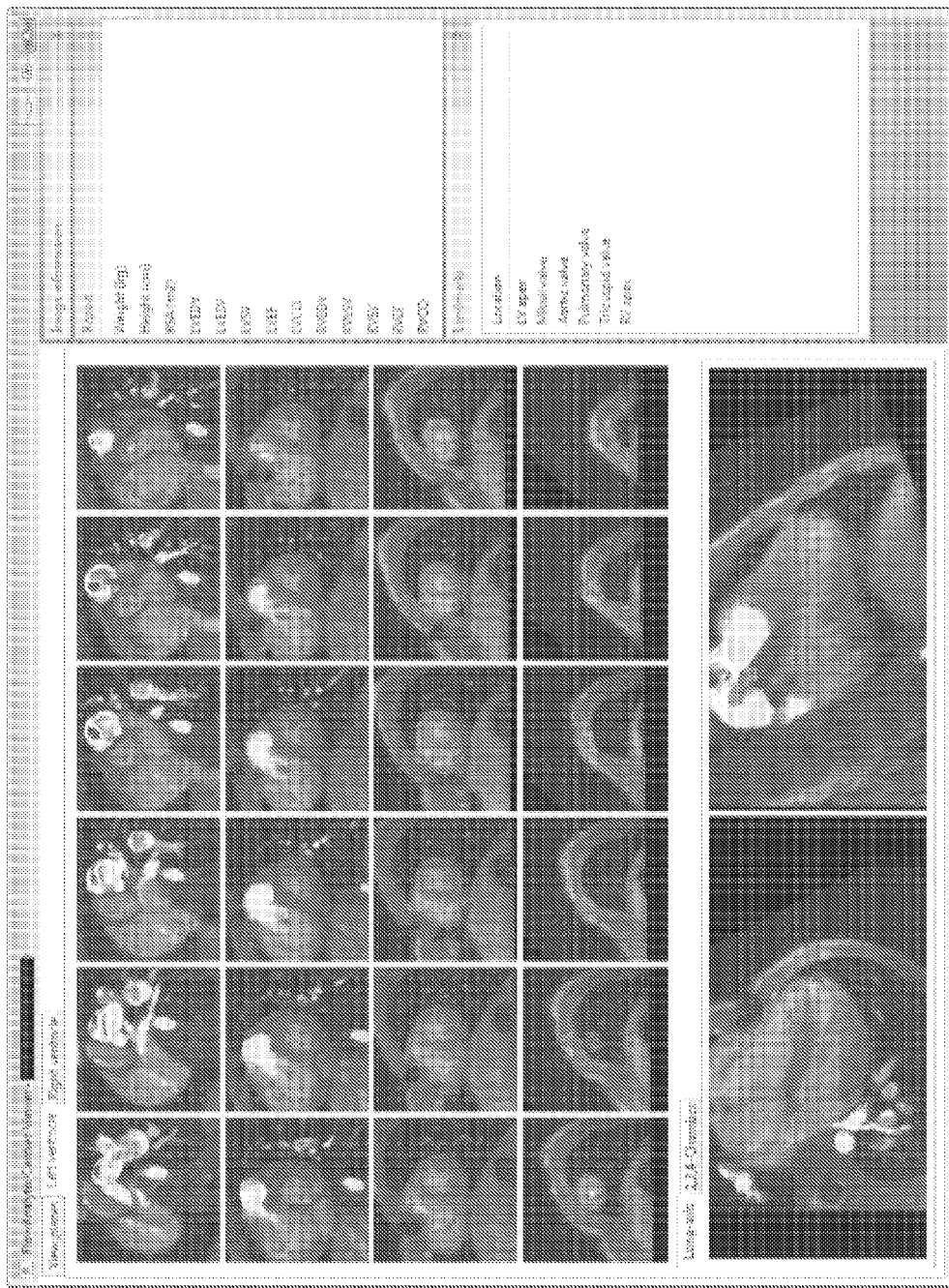
Figure 4C:
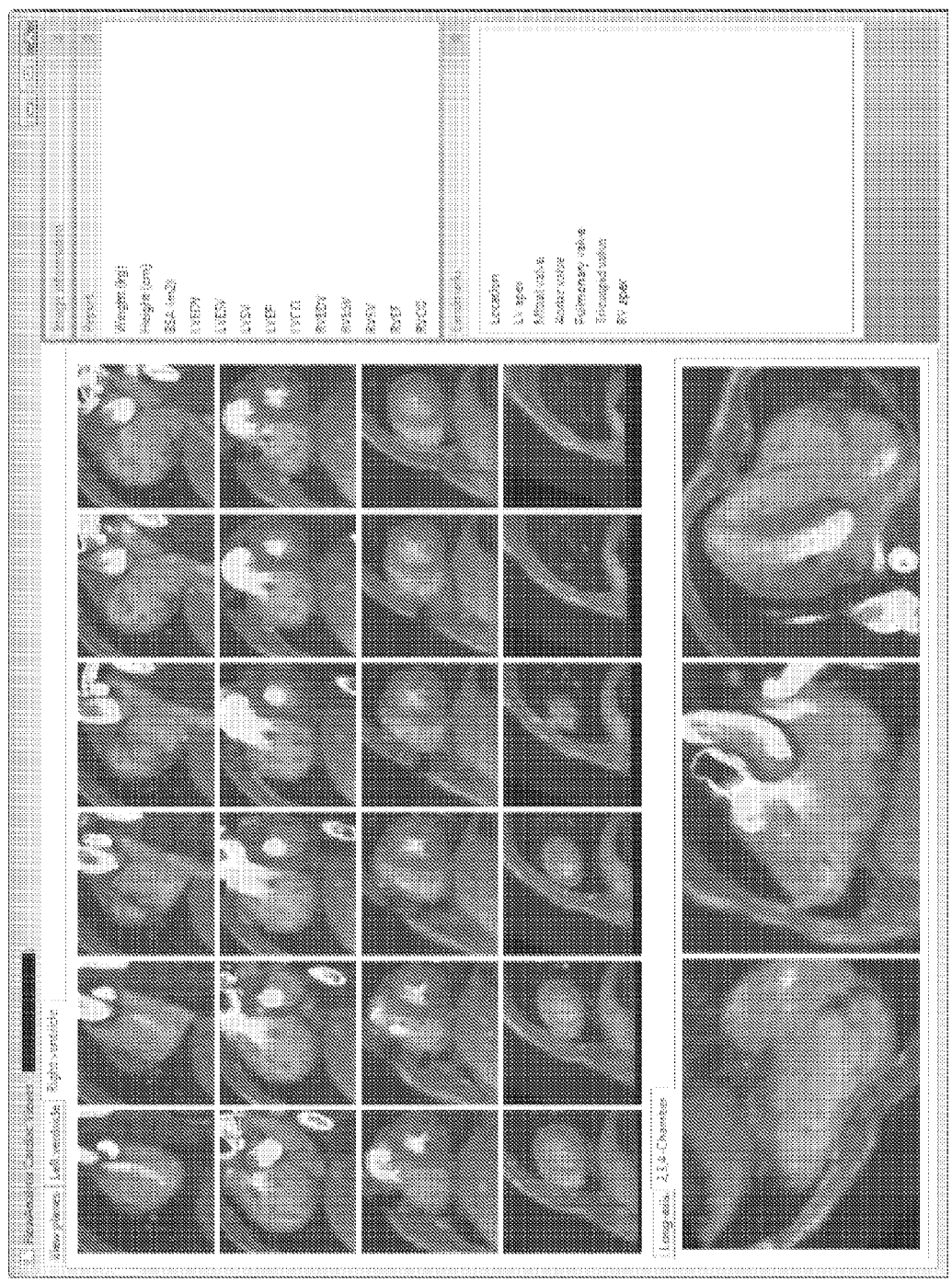
Figure 5A:
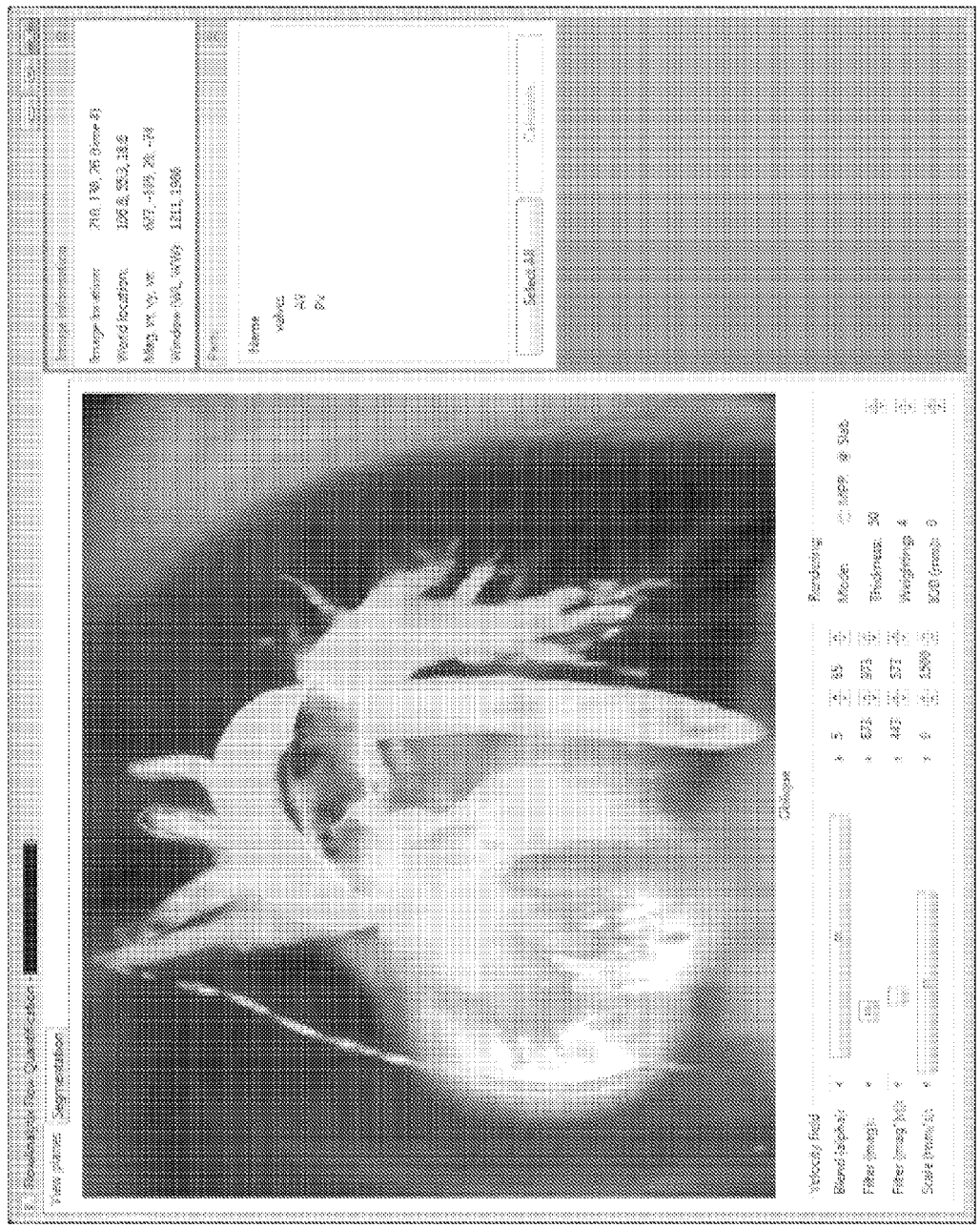
FIGS. 5A-D show screen captures of integrated volume rendering of magnitude (anatomic) and phase (velocity) data according an exemplary embodiment of the present invention. Multiple methods of rendering the anatomic data are readily accessible from the context menus including raysum (A), MIP (B), surface (C), and luminal (D) methods. Phase velocity data is automatically and dynamically superimposed on the anatomic rendering with a color transfer function that can be adjusted with sliders on the bottom of each window.
Figure 5B:
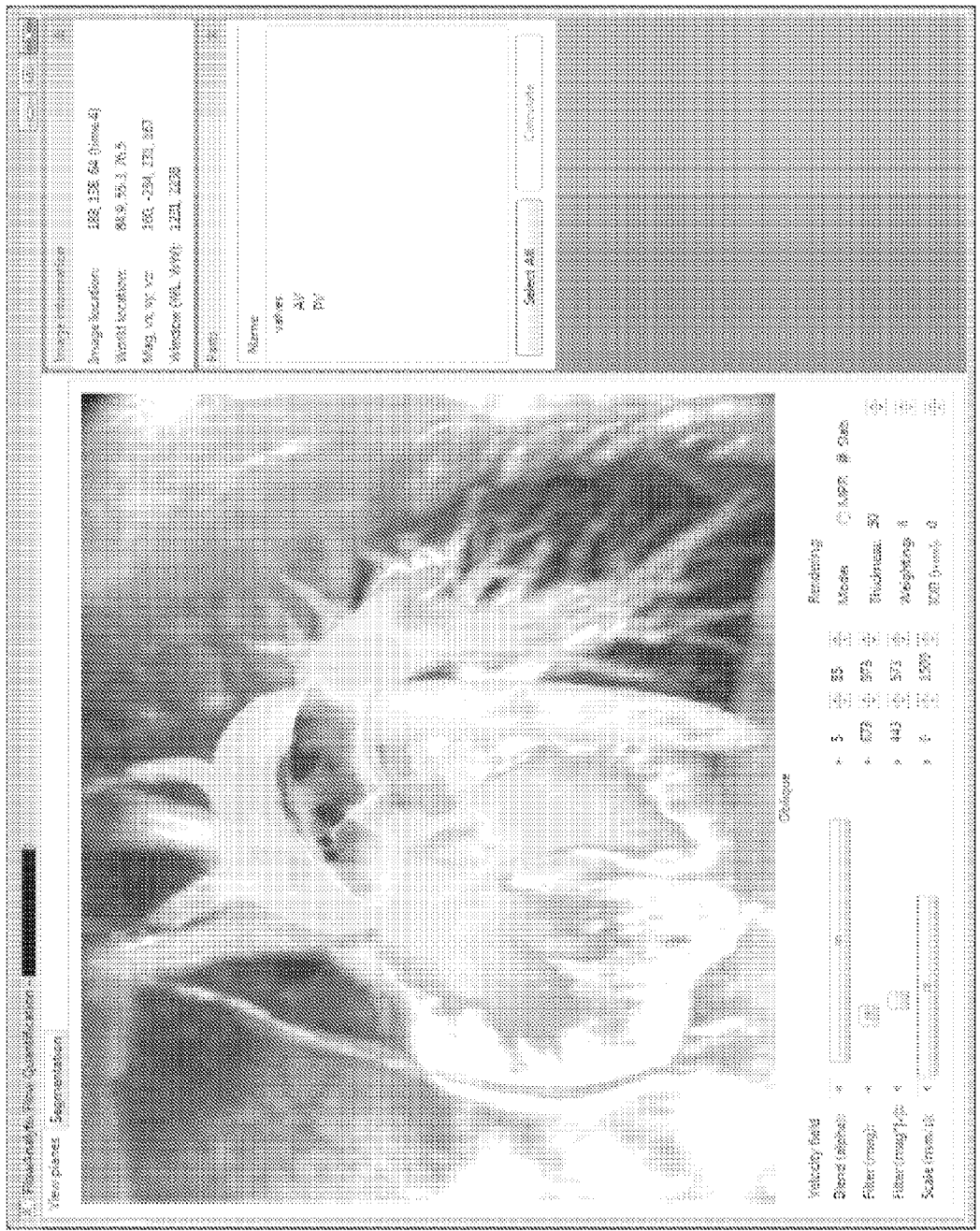
Figure 5C:
Figure 5D:
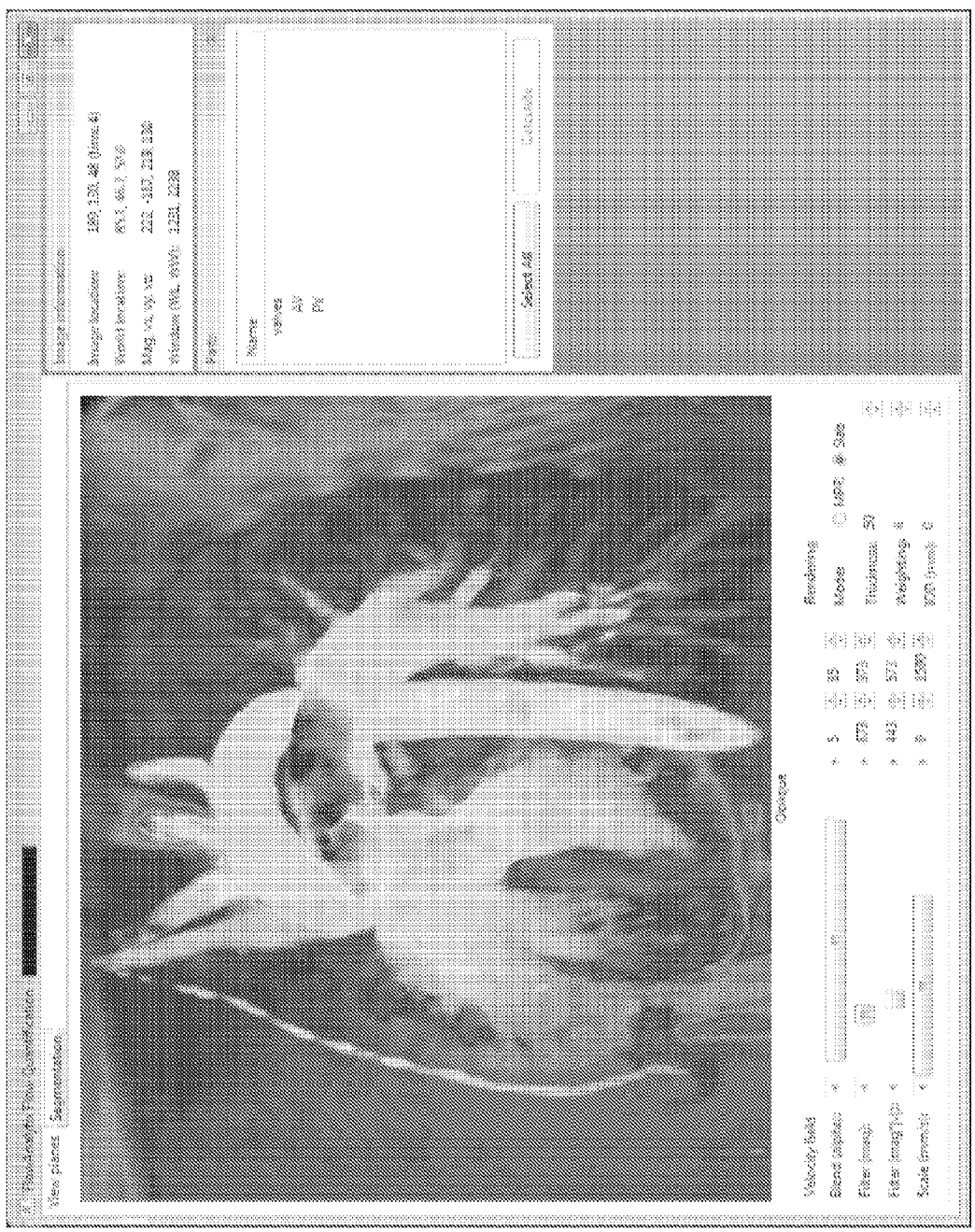

To compute an accurate model of background phase-error in phase-contrast MRI data, it is essential to accurately identify image voxels that are representative of static soft tissue. We enable accurate identification of a static soft tissue by using a combination of image filters:
1. Filter based on the signal intensity of anatomic (magnitude) images.
2. Filter based on a score that reflects the likelihood that a voxel represents "air or lung".
3. Filter based on a score that reflects the likelihood that a voxel represents "blood or moving tissue".

Since there is a certain amount of noise inherent in the acquired image data, it is often valuable to take advantage of the persistence of high signal in static tissues. Rather than filter each image at each temporal phase by the signal in that same temporal phase, we apply a filter based on the maximum signal intensity across all temporal time points. The user can then select the optimal signal intensity thresholds to suppress non-static tissue.

While signal intensity filters are helpful, these filters alone are insufficient to isolate voxels representative of static soft tissue. Further, it is difficult to define a single computed value from the image data that can specifically select voxels representative of static tissue. Instead, we define conceptually intuitive image filters that can be used to exclude (a) "air or lung" and (b) "blood" or "moving tissue", computed based on the anatomic (magnitude) and velocity (phase) image data.

To compute the "air or lung" filter, we have identified several features that are common to most pixels that typically represent "air or lung". These voxels typically have (a) low magnitude signal intensity, (b) high local relative spatial variation in the velocity field, and (c) low local coherence in the velocity field. We can therefore define a function that computes a summary score for "air or lung" at each position in space:

$$f_l(m, \vec{v}) = a(m) \cdot b(\vec{v}) \cdot [1 - c(\vec{v})].$$

where m represents magnitude (anatomic) image intensities, v represents the phase (velocity) vector field, a(m) represents the an estimate of the relative likelihood that the voxel is "air or lung" based on signal intensity alone, $$a(m) = \frac{m_{max} - m_0}{m_{max} - m_{min}} \cdot (1 - p_{min}) + p_{min}$$

computed based on the signal intensity of the magnitude image at each location, $m_0$, and arbitrary parameters $m_{min}$, $m_{max}$, $p_{min}$. The function b(v) represents the relative local spatial variation in the velocity field, $$b(\vec{v}) = \frac{stdev(|\vec{v}_0|)}{mean(|\vec{v}_0|)}$$

computed based on the velocity at each location, $\vec{v}_i$. The function c(v) represents a metric of local coherence in the velocity field, $$c(\vec{v}) = \sum_i w_i c_i(\vec{v})$$

computed as a weighted sum with arbitrary weights, $w_i$, of local coherence with nearby voxels, $$c_i(\vec{v}) = 1 - \frac{1}{\pi} \cos^{-1}\left(\frac{\vec{v}_0 \cdot \vec{v}_i}{|\vec{v}_0||\vec{v}_i|}\right)$$

where $v_0$ is the velocity at the current position in the image volume and $\vec{v}_i$ is the velocity in each nearby voxel.

To compute a "blood or moving tissue" filter, we have similarly identified features that are common to most voxels that represent these materials. These voxels typically have (a) high speed in the velocity field, (b) a characteristic signature in the Fourier transform of the temporal data, and (c) high local coherence in the velocity field. Often, these voxels also have high signal on the anatomic (magnitude) images as well, but this may vary depending on the utilization of intravenous contrast agents. We can therefore define a function that computes a summary score for "blood or moving tissue" at each position in space:

$$f_b(m, \vec{v}) = |\vec{v}_0| \cdot a(\vec{v}) \cdot c(\vec{v}).$$

where m represents magnitude (anatomic) image intensities, v represents the phase (velocity) vector field. The function a(v) represents a score based on the Fourier transform of temporal data at each position in the velocity field, $$a(\vec{v}) = \frac{b_{max} - b(\vec{v}_t)}{b_{max} - b_{min}} \cdot (1 - p_{min}) + p_{min}$$

computed based on the velocity over time at each location, $\vec{v}_t$, and arbitrary parameters $b_{min}$, $b_{max}$, $p_{min}$. The function b(v), $$b(v_t) = \sum_k \tilde{w}_k \, fft_k(v_t),$$

is computed as a weighted sum of the frequency components of velocity at each location. Excluding the first and last frequency components, voxels representative of "blood" typically have high values at the beginning and end of the frequency domain, while low in the middle. Thus, a useful weighting scheme for $\tilde{w}_k$ may look like (0, 1, 1, 1, 1, −1, −1, −1, −1, −1, −1, −1, 1, 1, 1, 0). The function c(v) again represents a metric of local coherence in the velocity field, as described in more detail above, $$c(\vec{v}) = \sum_i w_i c_i(\vec{v}).$$

Once an appropriate sub-volume of non-wrapped static tissue is selected, we can then use this subset of data to compute a model of eddy-current-related phase-offsets for the entire imaging volume. We specifically define a family of models that can be used to fully leverage the volumetric, three-dimensional nature of this data, namely, $$f_{n,m,l}(x,y,z) = h_x^n(x) \cdot h_y^m(y) \cdot h_z^l(z). \tag{4}$$

where n, m, l are non-negative integers and $h_x^n(x)$, $h_y^m(y)$ and $h_z^l(z)$ are the independent polynomial functions $$h_x^n(x) = \sum_{i=0}^n c_{x,i} x^i \tag{5a}$$

-continued $$h_y^m(y) = \sum_{i=0}^{m} c_{y,i} y^i \quad (5b)$$

$$h_z^l(z) = \sum_{i=0}^{l} c_{z,i} z^i \quad (5c)$$

The simplest usable model of this family is the three-dimensional, component-wise linear model, which we apply most commonly to volumetric phase-contrast MRI data obtained from a 1.5 T scanner.

$$f_{1,1,1}(x,y,z) = c_0 + c_x x + c_y y + c_z z + c_{xy} x \cdot y + c_{yz} y \cdot z + c_{xz} x \cdot z + c_{xyz} y \cdot z \quad (6)$$

Included within this family of eddy-current models is the sub-family of the form $g_{n,m,l}(x,y,z) = h_x^n(x) + h_y^m(y) + h_z^l(z)$. These can be derived by eliminating the cross-terms, which leaves us with a model that does not fully characterize the moments of eddy-current related phase-error that do not line up with the imaging axes. By analogy to Eq. 2 above, this simplified, but likely insufficient model is equivalently represented as $$g_{n,m,l}(x, y, z) = c_0 + \sum_{i=1}^{n} c_{x,i} x^i + \sum_{i=1}^{m} c_{y,i} y^i + \sum_{i=1}^{l} c_{z,i} z^i. \quad (7)$$

The parameters of the three-dimensional models proposed here can be estimated with least-squares regression using data from static tissues across the imaging volume. However, the identification of static voxels is imperfect, and can be more problematic in one temporal phase than another. We therefore choose to compute a single optimal three-dimensional model for all time points.

There are several efficient methods for creating an average model across all of the time points. The first method is to individually compute the parameters of a three-dimensional model at each time point, and then compute the average of each of the coefficients to arrive at a final model. The variance of the coefficients across time points can be a useful metric of the uncertainty. A second method is to compute the parameters of a three-dimensional model by fitting the mean phase across all of the time points for each static voxel in the volume. This approach will tend to average out outlier phase measurements, which otherwise could unfairly drive a least-squares regression. This is likely to be slightly more accurate than the first method. However, it is more difficult with this method to obtain an assessment of the degree of uncertainty in the coefficients of this model. A third method is to perform least-squares regression using static voxel data across all of the time points to arrive at a single model. This is the most memory-intensive approach, and potentially the least accurate of the three options.

The models and approaches that we have provided herein can be distinguished readily from prior methods by the use of an imaging volume instead of individual imaging planes to define the parameters of a three-dimensional phase-offset model. This new approach has several advantages. Since a three-dimensional model explicitly corrects for spatial variation in the slice direction, the changes in phase-offsets across slices can be corrected in a predictable manner. This approach is therefore less sensitive to errors in classifying static tissue. To further explore this point, its worthwhile to consider that there can be varying amounts of static tissue in each image slice. For example, in the mid-chest far fewer image voxels will represent static tissue than in the abdomen or upper chest. By using a volumetric approach, it is possible to obtain information about phase-errors in the mid-chest using data from the abdomen and upper chest.

The modeling approach we have applied also takes advantage of another property of the phase-error that has gone largely unutilized. By recognizing that the eddy-currents should affect each temporal phase equally, we chose a modeling approach that combines data from each of the temporal phases to further the improve accuracy of the model. This valuable assumption has not been accounted for in past approaches.

Vector Field Fusion Visualization

To facilitate time-efficient interpretation of high-dimensional volumetric phase-contrast MRI anatomic and vector field data, it is essential to combine and display the acquired information obtained in a way that can be quickly understood by the interpreting physician. Since such a large volume of information is acquired, and it can be difficult for a reader to interpret the medical images if the slices are too thin, it is important to provide a mechanism to perform multiple kinds of averaging (ray sum, maximum intensity projection, minimum intensity projection, surface rendering) across a slab of arbitrary thickness in the image volume, as has been implemented by a some existing software packages. This is commonly referred to in the medical imaging domain as "volume-rendering".

For optimal use of volumetric phase-contrast MRI data, vector field data also needs to be superimposed on these rendered anatomic images in a manner that does not completely obscure anatomic detail. The desired degree of superimposition may vary considerably between different examinations or different users. We therefore provide herein a user-interface mechanism that allows dynamic control of the opacity of the superimposed vector field data. In our implementation, this is done with a slider bar can be controlled by the user with variable width and start position. The start position of the slider bar establishes the minimum opacity, $o_{min}$ while the end position of the slider bar establishes the maximum opacity, $o_{max}$, values between 0 and 1.

A common strategy for assigning color to data from a medical image is to apply a transfer function. A slider bar with variable width and start position can be used to control the parameters of such a transfer function, such that a color $c_i$ can be assigned to each voxel based on its velocity, $\vec{v}_i$ $$c_i = \vec{f}(\vec{v}_i)$$

When velocity data lies below the start position of the slider bar, $v_{min}$, a the color at the minimum of the domain is assigned. When velocity data lies above the end position of the slider bar, $v_{max}$, a color at the maximum of the domain is assigned. Values in-between are interpolated along an arbitrary color scale.

It is important to recognize that not all of the vector field data is equally informative. In fact, excessive display of vector field data can be distracting and obscure medically important features in the imaging volume. We therefore provide herein a specific mechanism to increase the conspicuity of high quality velocity data using data masking and translucency, the parameters of which can controlled by the user. These user-controlled features can suppress low-quality vector field data while emphasizing high quality and diagnostically important vector field data. Two example masks that we currently implement are:
- a mask based solely on the signal magnitude, $m_i$
- a mask based on the product of signal magnitude and speed, $$\beta_i = m_i \cdot |\vec{v}_i|$$

For each of these masks, a slider bar can be controlled by the user with variable width and start position. When source image values lie below the start position of the slider, the velocity data is completely translucent and invisible on the display. When source image values lie above the end position of the slider, the velocity data is set to the maximum opacity. When source image values lie in-between, velocity data is partially transparent, with opacity levels linearly interpolated between the minimum and maximum opacity ($o_{min}$, $o_{max}$).

While it is fairly straightforward to superimpose the velocity field on a plane of data, it is not intuitive how to best perform this fusion across a volume. To maintain consistency with slider controls that adjust the opacity of the velocity field on the anatomic data during multiplanar reformatting visualization, we provide a running tab of the peak signal magnitude encountered in each volume-rendering projection so that they can be used to control the opacity of the volume-rendered vector field overlay relative to the volume-rendered anatomic image, $$m_{peak} = \max_i(m_i)$$
$$\beta_{peak} = \max_i(\beta_i)$$

We additionally devised a specific method that addresses this volume-rendering vector-field fusion problem, while simultaneously emphasizing pathologic features in the vector field. It is important to recognize that many pathologic conditions exhibit high-velocity flow. We therefore provide the use of velocity-weighting to increase conspicuity of this high-velocity data. As multiple iterations are typically performed in the volume rendering pipeline for the anatomic data, we provide a similar set of iterations that heavily weighs the opacity of high-velocity data, and define a, as the local velocity opacity at any given position:

$$\alpha_i = r_i^w$$

where w represents the weighting factor (usually values 4 or greater) and $r_i$ represents the speed scaled to the domain [0, 1], given by $$r_i = \begin{cases} 1, & |\bar{v}_i| > v_{max} \\ \dfrac{|\bar{v}_i|}{v_{max} - v_{min}}, & \text{otherwise} \end{cases}$$

At each iteration step in volume rendering, the local velocity opacity, $\alpha_i$, helps to govern the summary color vector, $\tilde{c}$, computed as $$\tilde{c} = \tilde{c} \cdot \left(1 - \frac{\alpha_i}{\tilde{\alpha}}\right) + c_i\left(\frac{\alpha_i}{\tilde{\alpha}}\right)$$

where the summary velocity opacity, $\tilde{\alpha}$, is iteratively updated by $$\tilde{\alpha} = \tilde{\alpha} + (1 - \tilde{\alpha}) \cdot \alpha_i$$

Due to the high dimensionality of the volumetric phase-contrast MRI data, we believe it is valuable to take advantage of stereoscopic 3D visualization techniques to optimize the efficiency of interpretation of this data. By providing this method of visualization, the conspicuity of anatomic and velocity noise can be dispersed across the displayed volume, preventing noise from obscuring important diagnostic details in the data. The optimal method to incorporate this technology into the rendering pipeline and while minimizing the impact on the interface of a diagnostic software is not immediately clear. We therefore provide herein a specific pipeline that enables stereoscopic visualization with the minimum amount of user intervention.

1. User enables/disables stereoscopic visualization with a single button click.
2. User manipulates an interocular distance (IOD) control to adjust the amplitude of stereoscopic visualization.
3. Computer generates independent views for each eye based on the IOD parameter.

When stereoscopic visualization is enabled, the orientation of independent views from each eye can be directly calculated based on a fixed view distance, d, and the IOD parameter, iod. There are multiple methods for obtaining an angled projection from these two parameters, but we provide the following as one method:

1. Compute an angle of viewing for each eye, $$\theta_e = \arctan\left(\frac{iod}{2}, d\right)$$

For the right eye, $\theta_r = \theta_e$ and for the left eye, $\theta_l = -\theta_e$ 2. Compute the eye position, $\vec{p}_e$, from the center of the viewing plane, $\vec{p}_o$ $$\vec{p}_e = \vec{p}_o + \sqrt{d^2 + iod^2} \cdot R_\theta \hat{n}$$

3. For each position in the rendered image, compute an eye projection vector based on the difference between the eye position and the image position.
4. Volume rendering of a slab of fixed thickness can then be performed as previously described along each eye projection vector.

Vector Field Plane Selection

We have determined that one of the most important diagnostic tasks required for the quantitative evaluation of the heart and blood vessels is the precise placement of specific imaging planes that can be used to make measurements of the vector field. Without adequate visualization tools, placement of these planes is extremely challenging, and thus the visualization approaches described above are essential for performance of this task. It is important not only to place these planes precisely, but to do so with the minimum amount of user effort or interaction.

In combination with the vector field fusion visualization approaches we describe above, we provide a single-button interactive method for initial placement and orientation of an optimal plane. At the time of the single-button event, the location of the pointer on the display specifies the center of the plane. The value of the vector field at and near that location can then be used to specify the orientation (normal vector) of the plane. In other words, the plane defined by the single-click event can be described by as all points $\vec{x}$ that satisfy $$\vec{v}(\vec{p})\cdot(\vec{x} - \vec{p}_i) = 0$$

where $\vec{p}$ is the location of the pointer in the image, $\vec{v}(\vec{p})$ is the value of the vector field at that location. Once this initial position and orientation is established, the plane can be repositioned or reoriented using cross-reference lines and markers that appear on other planes of imaging.

Another important task that is necessary for comprehensive evaluation of the heart and vessels is the placement of dynamic (moving) imaging planes. It is not immediately clear what the best way is for a user to specify the position and orientation of such a plane across multiple time points of data. We thus provide herein a procedure that minimizes the effort required to specify a dynamic plane. This procedure enables a user to perform a series of steps for full specification of a dynamic plane:

1. User places an initial static plane with a particular position and orientation.
2. User traverses to another time point in the data set.
3. User repositions and reorients the plane in this new time point.
4. Computer automatically creates intermediate planes for time points in-between with positions and normal vectors that are linearly interpolated between the user-specified planes.
5. Computer automatically displays data in the dynamically specified plane.
6. Repeat steps 2-5.

Visualization-Assisted Cardiac Structure and Vessel Segmentation

Once static or dynamic planes are specified by a user, the boundaries of any given structure or vessel of interest need to be delineated or "segmented".

This generally requires extensive user-input to delineate the boundaries of the structure of interest for all time-points of data acquired. To minimize this otherwise time-intensive effort, in one example we use automatic interpolation in-between time points where boundaries of a structure are specifically defined. Any number of closed-polygon interpolation methods can be used. This enables an abbreviated procedure for full delineation of the boundaries of a given structure.

1. Computer generates a view of the data in the plane previously specified by the user.
2. User draws a boundary around a structure of interest (i.e. aorta, pulmonary artery).
3. User traverses to another time point in the data set.
4. Computer generates a view of the data in the plane previously specified by the user with the boundary superimposed on the image.
5. User draws or updates the boundary around a structure of interest.
6. Computer automatically generates interpolated boundaries for the time points in-between.
7. Repeat steps 3-6, as needed.

Both the anatomic and vector field data acquired in the volumetric phase-contrast MRI acquisition can provide detail about the appropriate boundaries of vessels and cardiac structures. We recognized that while both of these are independently informative, velocity field fusion rendering can also benefit the accuracy of segmentation of these anatomic structures. For this reason, we provide the use of color and vector fusion rendering methods described above to further improve accuracy. This is enabled by allowing the user to perform segmentation directly on these fusion images.

While fusion images are very valuable for segmentation, they can hide artifacts in the underlying image data, especially when color transfer function does not incorporate directionality of motion. This is specifically a problem when phase-aliasing is present in the vector field data. The presence of artifact can negatively impact the accuracy of blood flow measurements. In order to emphasize the presence of phase (velocity) aliasing, we provide simultaneous display of nearest-neighbor rendered images. This allows users to readily detect the presence of artifact and select an alternate plane of data to perform quantification.

While we have found that rendering color velocity fusion and nearest-neighbor interpolations side-by-side can help interpreting physicians quickly identify aliasing, the process of looking at these separate images is likely to slow down the efficiency of interpretation and segmentation of the volumetric phase-contrast imaging data. We therefore provide an additional, alternate method of encapsulating the directional information that can be obscured with certain color transfer functions. By superimposing arrows over the rendered images described thus far, this directional information can be quickly and more efficiently integrated into the users understanding of the underlying data set. We provide the following set of requirements for the superimposed arrows to maintain simplicity of the software interface:

1. Length and/or size of arrows proportionate to the length of the velocity vector.
2. Masking of arrows governed using similar or same controls governing the masking of the color overlay.
3. Opacity of arrows governed using similar or same controls governing the opacity of the color overlay.

Once segmentations are performed in the locations and imaging planes desired by the user, a computer can readily compute any number of derived values from the vector field. This not only includes quantification of volumetric blood flow, but also voracity, shear stress, pressure, and turbulence, which may be computed from the velocity vector field using the Navier-Stokes governing equations.

Landmark-Based Conventional Cardiac Plane Visualization

Freehand interactive navigation of a volume of data can be challenging for some physicians who will be involved in interpreting the data acquired from volumetric phase-contrast MRI. It is therefore important to provide additional intuitive mechanisms for achieving conventional imaging views that are more familiar to these interpreting physicians. During the acquisition of a conventional cardiac MRI, the specification of these conventional imaging views (right and left two-chamber, right and left three-chamber, four-chamber, right and left short axis) are usually performed on the MRI scanner by translating and rotating reference lines superimposed on images in other planes. This process can be mirrored in software for placing planes in volumetric CT or MRI data, but remains time-consuming. Further, it is not possible with this approach to describe a dynamic view that can track the changing orientation of the heart. We therefore provide an alternate approach enabled by user-specification of temporally-resolved landmarks.

1. User marks a location on the image with a label (i.e. left ventricular apex, right ventricular apex, mitral valve, tricuspid valve, aortic valve, pulmonary valve, anterior papillary muscle, posterior papillary muscle)
2. Computer displays a marker (i.e. an 'x') superimposed over the image data that represents that location, which can be moved by the user to a different location.
3. User traverses to another time point in the data set.
4. User modifies the location of the marker to a different location.
5. Computer updates the display to reflect new location
6. Computer automatically interpolates the position of the marker for all time points in-between defined markers.
7. Repeat steps 3-6, as needed.

Once a sufficient set of landmarks are defined, specialized cardiac views can then be automatically computed based on these locations. For example, the left ventricular three-chamber view can be defined by three points, the left ventricular apex, center of the mitral valve, and center of the aortic valve. Since each of these locations can change over time, the orientation of conventional static planes that are typically used in cardiac MRI, CT, or ECHO can be suboptimal, especially if the axes of the heart change significantly during the course of the cardiac cycle. To overcome this problem, we use temporally-resolved landmarks to specify dynamic cardiac view planes, which translate and rotate according to the position of each of the landmarks at each time point. For example, for the left ventricular three-chamber view, the dynamic plane at each time point can be described as all points $\vec{x}$ that satisfy $$(\vec{a}-\vec{b})\times(\vec{b}-\vec{c})\cdot\left(\vec{x}-\frac{\vec{a}+\vec{b}+\vec{c}}{3}\right)=0$$

where $\vec{a}$ is the location of the aortic valve, $\vec{b}$ is the location of the left ventricular apex, and $\vec{c}$ is the location of the mitral valve.

We recognized that it is sometimes difficult to precisely place the location of some landmarks on conventional imaging planes. Once approximate cardiac views have been obtained however, manual tuning these landmarks can be much easier for users to perform. In one example, we use the following procedure to fine-tune the cardiac views:

1. Computer displays initial cardiac views based on landmarks as described above.
2. Computer displays markers superimposed on these cardiac views.
3. User modifies the location of the marker on one of the views.
4. Computer automatically updates all cardiac views dependent on the location of the modified marker.
5. Computer automatically interpolates the position of the marker for all time points in-between defined markers.
6. Computer automatically updates all cardiac views dependent on the location of the modified marker for affected time points.
7. User traverses to another time point in the data set.
8. Repeat steps 1-8, as needed.

The quantification of ventricular volumes from cardiac MRI requires consistent delineation of the boundary between the wall of the ventricle and the lumen. This is an imprecise art, dependent not only on the quality of the contrast difference between the wall of the ventricle and the lumen, but also the three-dimensional registration of anatomic structures that may not be readily apparent on any single plane of view. In addition, user-delineation of the boundary is also a time-intensive effort if every time point or slice needs to be separately segmented. Instead, in one example, we use a series of procedures that enables more consistent and reliable segmentation of the boundaries of the ventricles.

1. Computer displays each of the short axis and long-axis (2-, 3-, 4-chamber) views with landmark markers superimposed on these cardiac views.
2. User draws a boundary around a structure of interest (i.e. ventricular wall).
3. User selects another time point or slice in the data set.
4. Computer updates display each of the short axis and long-axis (2-, 3-, 4-chamber) views with landmark markers and delineated boundaries superimposed on these cardiac views.
5. User draws or updates a boundary around a structure of interest (i.e. ventricular wall).
6. Computer automatically generates interpolated boundaries for slices and/or time points in-between.
7. Repeat steps 3-6, as needed.

Once segmentations of the boundaries of the structure of interest are specified in more than one slice, an estimate of the volume of the structure can be readily computed based on the relationship between the areas contained within each boundary, $A_j$, and the spacing between slices used to perform the segmentation (usually short-axis), $\Delta_j$. For example, in the simplest case, one can compute a Riemann sum to obtain an estimate of the volume, V, $$V=\sum_j A_j \cdot \Delta_j$$

Aspects of the invention can be computer-implemented software, modules or pipelines executable by a computer system either as a stand-alone package or integrated with an imaging device or system.

REFERENCES

1. Gatehouse P D, Rolf M P, Graves M J, et al. Flow measurement by cardiovascular magnetic resonance: a multi-centre multi-vendor study of background phase offset errors that can compromise the accuracy of derived regurgitant or shunt flow measurements. J Cardiovasc Magn Reson; 12(1):5.
2. Kilner P J, Gatehouse P D, Firmin D N. Flow measurement by magnetic resonance: a unique asset worth optimising. J Cardiovasc Magn Reson. 2007; 9(4):723-8.
3. Chernobelsky A, Shubayev O, Comeau C R, Wolff S D. Baseline correction of phase contrast images improves quantification of blood flow in the great vessels. J Cardiovasc Magn Reson. 2007; 9(4):681-5.
4. Walker P G, Cranney G B, Scheidegger M B, Waseleski G, Pohost G M, Yoganathan A P. Semiautomated method for noise reduction and background phase error correction in MR phase velocity data. Journal of Magnetic Resonance Imaging. 1993; 3(3):521-30.
5. Lankhaar J W, Hofman M B, Marcus J T, Zwanenburg J J, Faes T J, Vonk-Noordegraaf A. Correction of phase offset errors in main pulmonary artery flow quantification. J Magn Reson Imaging. 2005; 22(1):73-9.

What is claimed is:

1. A method of operation in at least one component of a medical imaging system that employs volumetric phase-contrast magnetic resonance imaging (MRI) data, the method comprising:
   receiving volumetric phase-contrast MRI data that includes a plurality of voxels;
   identifying at least one set of voxels that represent static soft tissue;
   generating via at least one computer at least one eddy current related phase offset based on the at least one set of voxels that represent static soft tissue; and
   performing a phase error correction based at least in part on the generated at least one eddy current related phase offset,
   wherein identifying at least one set of voxels that represent static soft tissue includes:

applying a first filter to the volumetric phase-contrast MRI data, the first filter based on an intensity value of a magnitude associated with the voxels of the volumetric phase-contrast MRI data;

applying a second filter to the volumetric phase-contrast MRI data, application of the second filter which excludes air and lung tissue from the volumetric phase-contrast MRI data; and applying a third filter to the volumetric phase-contrast MRI data, application of the third filter which excludes blood and other moving tissue from the volumetric phase-contrast MRI data.

2. The method as set forth in claim 1, wherein applying a first filter includes applying the first filter which is based on a maximum signal intensity across all of a plurality of temporal time points represented in the volumetric phase-contrast MRI data.

3. The method as set forth in claim 1, further comprising receiving at least one user input indicative of at least one signal intensity threshold to suppress non-static tissue via application of the first filter.

4. The method as set forth in claim 1, further comprising generating an average model across all temporal time points for an imaging volume represented in the volumetric phase-contrast MRI data.

5. The method as set forth in claim 4, wherein generating an average model across all temporal time points includes individually computing a number of parameters of a three-dimensional model at each temporal time point, and computing an average of each of a number of coefficients of the three-dimensional model.

6. The method as set forth in claim 4, wherein generating an average model across all temporal time points includes computing a number of parameters of a three-dimensional model by fitting a mean phase across all of the temporal time points for each static voxel in the imaging volume represented in the volumetric phase-contrast MRI data.

7. The method as set forth in claim 4, wherein generating an average model across all temporal time points includes performing a least squares regression using static voxel data across all of the temporal time points represented in the volumetric phase-contrast MRI data.

8. A method of operation in at least one component of a medical imaging system that employs volumetric phase-contrast magnetic resonance imaging (MRI) data, the method comprising:

receiving volumetric phase-contrast MRI data that includes a plurality of voxels;

identifying at least one set of voxels that represent static soft tissue;

generating via at least one computer at least one eddy current related phase offset based on the at least one set of voxels that represent static soft tissue; and performing a phase error correction based at least in part on the generated at least one eddy current related phase offset, wherein identifying at least one set of voxels that represent static soft tissue includes:

applying a first filter to the volumetric phase-contrast MRI data, the first filter based on an intensity value of a magnitude associated with the voxels of the volumetric phase-contrast MRI data;

applying a second filter to the volumetric phase-contrast MRI data, application of the second filter which excludes air and lung tissue from the volumetric phase-contrast MRI data; and applying a third filter to the volumetric phase-contrast MRI data, application of the third filter which excludes blood and other moving tissue from the volumetric phase-contrast MRI data, and wherein applying a second filter to exclude air and lung tissue includes applying the second filter which is based on a relationship $f_1(m, \vec{v}) = a(m) \cdot b(\vec{v}) \cdot [1 - c(\vec{v})]$, where m is magnitude image intensities, $\vec{v}$ phase (velocity vector field), and $a(m)$ an estimate of a relative likelihood that a given voxel is air or lung based on signal intensity alone.

9. The method as set forth in claim 8, wherein $$a(m) = \frac{m_{max} - m_0}{m_{max} - m_{min}} \cdot (1 - p_{min}) + p_{min}$$

is computed based on a signal intensity of the magnitude image at each location $m_0$, and the function $$b(\vec{v}) = \frac{stdev(|\vec{v}_0|)}{mean(|\vec{v}_0|)}$$

computed based on a velocity at each location.

10. The method as set forth in claim 8, wherein $$c_i(\vec{v}) = 1 - \frac{1}{\pi} \cos^{-1}\left(\frac{\vec{v}_0 \cdot \vec{v}_i}{|\vec{v}_0||\vec{v}_i|}\right)$$

where $\vec{v}_0$ is the velocity at a current position in the image volume and $\vec{v}_i$ is the velocity in each nearby voxel.

11. A method of operation in at least one component of a medical imaging system that employs volumetric phase-contrast magnetic resonance imaging (MRI) data, the method comprising:

receiving volumetric phase-contrast MRI data that includes a plurality of voxels;

identifying at least one set of voxels that represent static soft tissue;

generating via at least one computer at least one eddy current related phase offset based on the at least one set of voxels that represent static soft tissue; and performing a phase error correction based at least in part on the generated at least one eddy current related phase offset, wherein identifying at least one set of voxels that represent static soft tissue includes:

applying a first filter to the volumetric phase-contrast MRI data, the first filter based on an intensity value of a magnitude associated with the voxels of the volumetric phase-contrast MRI data;

applying a second filter to the volumetric phase-contrast MRI data, application of the second filter which excludes air and lung tissue from the volumetric phase-contrast MRI data; and applying a third filter to the volumetric phase-contrast MRI data, application of the third filter which excludes blood and other moving tissue from the volumetric phase-contrast MRI data, and wherein applying a third filter to exclude blood and other moving tissue includes applying the third filter which is based on a relationship $f_b(m, \vec{v}) = |\vec{v}_0| \cdot a(\vec{v}) \cdot c(\vec{v})$, where m represents magnitude image intensities, $\vec{v}$ represents the phase (velocity) vector field, $a(\vec{v})$ represents a score based on a Fourier transform of temporal data at each position in the velocity field.

12. The method as set forth in claim 11, wherein $$a(\vec{v}) = \frac{b_{max} - b(\vec{v}_t)}{b_{max} - b_{min}} \cdot (1 - p_{min}) + p_{min}.$$

13. The method as set forth in claim 12, wherein $$b(v_t) = \sum_k w_k \mathit{fft}_k(v_t).$$

14. The method as set forth in claim 11, wherein $$c(\vec{v}) = \sum_i w_i c_i(\vec{v}).$$

15. At least one component of a medical imaging system that employs volumetric phase-contrast magnetic resonance imaging (MRI) data, the at least one component comprising:
a computer, that in use:
receives volumetric phase-contrast MRI data that includes a plurality of voxels;
identifies at least one set of voxels that represent static soft tissue;
generates at least one eddy current related phase offset based on the at least one set of voxels that represent static soft tissue; and
performs a phase error correction based at least in part on the generated at least one eddy current related phase offset,
wherein to identify at least one set of voxels that represent static soft tissue, the computer:
applies a first filter to the volumetric phase-contrast MRI data, the first filter based on an intensity value of a magnitude associated with the voxels of the volumetric phase-contrast MRI data;
applies a second filter to the volumetric phase-contrast MRI data, application of the second filter which excludes air and lung tissue from the volumetric phase-contrast MRI data; and
applies a third filter to the volumetric phase-contrast MRI data, application of the third filter which excludes blood and other moving tissue from the volumetric phase-contrast MRI data.

16. The at least one component as set forth in claim 15, wherein the computer applies the first filter which is based on a maximum signal intensity across all of a plurality of temporal time points represented in the volumetric phase-contrast MRI data.

17. The at least one component as set forth in claim 15, wherein the computer further:
receives at least one user input indicative of at least one signal intensity threshold to suppress non-static tissue via application of the first filter.

18. At least one component of a medical imaging system that employs volumetric phase-contrast magnetic resonance imaging (MRI) data, the at least one component comprising:
a computer, that in use:
receives volumetric phase-contrast MRI data that includes a plurality of voxels;
identifies at least one set of voxels that represent static soft tissue;
generates at least one eddy current related phase offset based on the at least one set of voxels that represent static soft tissue; and
performs a phase error correction based at least in part on the generated at least one eddy current related phase offset,
wherein to identify at least one set of voxels that represent static soft tissue, the computer:
applies a first filter to the volumetric phase-contrast MRI data, the first filter based on an intensity value of a magnitude associated with the voxels of the volumetric phase-contrast MRI data;
applies a second filter to the volumetric phase-contrast MRI data, application of the second filter which excludes air and lung tissue from the volumetric phase-contrast MRI data; and
applies a third filter to the volumetric phase-contrast MRI data, application of the third filter which excludes blood and other moving tissue from the volumetric phase-contrast MRI data, wherein the computer applies the third filter which is based on a relationship $f_b(m, \vec{v}) = |\vec{v}_0| \cdot a(\vec{v}) \cdot c(\vec{v})$, where m represents magnitude image intensities, $\vec{v}$ represents the phase (velocity) vector field, $a(\vec{v})$ represents a score based on a Fourier transform of temporal data at each position in the velocity field, and wherein:

$$a(\vec{v}) = \frac{b_{max} - b(\vec{v}_t)}{b_{max} - b_{min}} \cdot (1 - p_{min}) + p_{min},$$

$$b(v_t) = \sum_k w_k \mathit{fft}_k(v_t), \text{ and}$$

$$c(\vec{v}) = \sum_i w_i c_i(\vec{v}).$$

19. The at least one component as set forth in claim 15, wherein the computer further generates an average model across all temporal time points for an imaging volume represented in the volumetric phase-contrast MRI data.

20. The at least one component as set forth in claim 19, wherein to generate an average model across all temporal time points the computer individually computes a number of parameters of a three-dimensional model at each temporal time point, and computes an average of each of a number of coefficients of the three-dimensional model.

21. The at least one component as set forth in claim 19, wherein to generate an average model across all temporal time points the computer computes a number of parameters of a three-dimensional model by fitting a mean phase across all of the temporal time points for each static voxel in the imaging volume represented in the volumetric phase-contrast MRI data.

22. The at least one component as set forth in claim 19, wherein to generates an average model across all temporal time points the computer performs a least squares regression using static voxel data across all of the temporal time points represented in the volumetric phase-contrast MRI data.

23. At least one component of a medical imaging system that employs volumetric phase-contrast magnetic resonance imaging (MRI) data, the at least one component comprising:
 a computer, that in use:
  receives volumetric phase-contrast MRI data that includes a plurality of voxels;
  identifies at least one set of voxels that represent static soft tissue;
  generates at least one eddy current related phase offset based on the at least one set of voxels that represent static soft tissue; and
  performs a phase error correction based at least in part on the generated at least one eddy current related phase offset,
  wherein to identify at least one set of voxels that represent static soft tissue, the computer:
  applies a first filter to the volumetric phase-contrast MRI data, the first filter based on an intensity value of a magnitude associated with the voxels of the volumetric phase-contrast MRI data;
  applies a second filter to the volumetric phase-contrast MRI data, application of the second filter which excludes air and lung tissue from the volumetric phase-contrast MRI data; and
  applies a third filter to the volumetric phase-contrast MRI data, application of the third filter which excludes blood and other moving tissue from the volumetric phase-contrast MRI data, and
  wherein to apply a second filter to exclude air and lung tissue the computer applies the second filter which is based on a relationship $f_1(m, \vec{v}) = a(m) \cdot b(\vec{v}) \cdot [1 - c(\vec{v})]$, where m is magnitude image intensities, $\vec{v}$ phase (velocity vector field), and a(m) an estimate of a relative likelihood that a given voxel is air or lung based on signal intensity alone.

24. The method as set forth in claim 23, wherein $$a(m) = \frac{m_{max} - m_0}{m_{max} - m_{min}} \cdot (1 - p_{min}) + p_{min}$$

is computed based on a signal intensity of the magnitude image at each location $m_0$, and the function $$b(\vec{v}) = \frac{stdev(|\vec{v}_0|)}{mean(|\vec{v}_0|)}$$

computed based on a velocity $\vec{v}_i$ at each location, and $$c_i(\vec{v}) = 1 - \frac{1}{\pi}\cos^{-1}\left(\frac{\vec{v}_0 \cdot \vec{v}_i}{|\vec{v}_0||\vec{v}_i|}\right)$$

where $\vec{v}_0$ is the velocity at a current position in the image volume and is the velocity in each nearby voxel.

* * * * *